United States Patent [19]

Krantz et al.

[11] Patent Number: 5,755,231
[45] Date of Patent: May 26, 1998

[54] TEST STRIP INCLUDING INTEGRAL SPECIMEN FLOW RETARDING STRUCTURE

[75] Inventors: Gary Krantz, Laguna Beach; Shuenn-Tzong Chen, Irvine; Adam Zipp, Laguna Hills; Joanne Zeng, Santa Ana, all of Calif.

[73] Assignee: Plus Bio, Inc., Irvine, Calif.

[21] Appl. No.: 442,672

[22] Filed: May 17, 1995

[51] Int. Cl.⁶ ........................................................ A61B 5/00
[52] U.S. Cl. ..................................... 128/771; 128/760
[58] Field of Search ................................. 128/771, 760; 422/56, 57; 435/11, 14; 436/95, 169, 170

[56] References Cited

U.S. PATENT DOCUMENTS

| | | | |
|---|---|---|---|
| 3,552,928 | 1/1971 | Fetter | 422/56 |
| 3,783,105 | 1/1974 | Moyer et al. | 435/287.8 |
| 3,992,158 | 11/1976 | Przybylowicz | 422/57 |
| 4,110,079 | 8/1978 | Schaeffer et al. | 422/56 |
| 4,258,001 | 3/1981 | Pierce et al. | 422/56 |
| 4,362,697 | 12/1982 | Tabb et al. | 422/56 |
| 4,477,575 | 10/1984 | Vogel et al. | 436/170 |
| 4,637,978 | 1/1987 | Dappen | 435/11 |
| 4,732,736 | 3/1988 | Kobayashi et al. | 422/56 |
| 4,780,411 | 10/1988 | Piejko et al. | 422/56 |
| 4,790,979 | 12/1988 | Terminiello et al. | 128/771 |
| 4,832,797 | 5/1989 | Vadgama et al. | 204/1 |
| 4,883,764 | 11/1989 | Kloepfer | 422/56 |
| 4,886,740 | 12/1989 | Vadgama et al. | 435/4 |
| 4,906,371 | 3/1990 | Miller | 210/321.61 |
| 4,919,767 | 4/1990 | Vadgama et al. | 435/4 |
| 4,935,346 | 6/1990 | Phillips et al. | 435/14 |
| 4,994,238 | 2/1991 | Daffern et al. | 422/56 |
| 5,304,468 | 4/1994 | Phillips et al. | 435/14 |
| 5,393,493 | 2/1995 | Makino et al. | 422/57 |
| 5,437,973 | 8/1995 | Vadgama et al. | 435/4 |
| 5,460,974 | 10/1995 | Kozak et al. | 422/57 |

FOREIGN PATENT DOCUMENTS 0 141 648 A2   5/1985   European Pat. Off. .

*Primary Examiner*—Michael Buiz
*Assistant Examiner*—Patrick W. Rasche
*Attorney, Agent, or Firm*—Gregory Garmong

[57] ABSTRACT

A test strip includes a first layer and an overlying differential flow-retarding layer that reduces the fraction of a component of a liquid specimen percolated therethrough. An inert backing, preferably having an aperture therethrough, overlies the flow-retarding layer. For the testing of a blood specimen, the flow-retarding layer is formed of glass fibers that reduce the fraction of red blood cells in the percolate, leaving primarily, but not entirely, plasma in the percolate. The first layer includes chemicals that react with a component of the plasma such as glucose in a measurable reaction, preferably a visually measurable reaction. In using this test strip, the blood specimen is placed into the aperture of the backing and permitted to percolate through the flow-retarding layer such that a fraction of the red blood cells is removed from the percolate. The chemicals in the first layer react with the glucose in the plasma to produce a change that is visually measurable from the bottom side of the active layer with reduced visual interference from the red color of whole blood on the bottom side of the reaction layer.

10 Claims, 4 Drawing Sheets

TEST STRIP INCLUDING INTEGRAL SPECIMEN FLOW RETARDING STRUCTURE

BACKGROUND OF THE INVENTION

This invention relates to a test strip for use in testing a liquid specimen, and, more particularly, to a test strip of particular value in optical reflectance testing for the amount of glucose in blood by contacting a specimen of the blood to the test strip.

A reagent-containing test strip provides a convenient and easy approach for conducting certain types of chemical analyses. The test strip is normally prepared by impregnating a layer of a porous material with a solution containing the reagent, and optionally other ingredients, to produce a reagent layer. This step is readily accomplished by dipping the porous material into the reagent solution. The test strip and solution are dried to fix the reagent in the porous material. Additional reagents may be added by impregnating the porous layer with additional solutions containing the additional reagents and drying the porous material after each further treatment, or by supplying the additional reagents in separate layers.

To conduct a test using the test strip, a liquid specimen that may contain an active species is contacted to the test strip. The liquid dissolves reagents that were previously introduced into the porous material of the reagent layer, so that these reagents can mix with each other and with the active species, if present. The subsequent reaction is selected to cause some measurable change in the test strip. For example, if one of the reagents is a dye, the test strip can be made to change color responsive to the presence of the reactive species in the liquid specimen.

A test strip may be used in several ways. One common approach is to dip the test strip into a specimen of the liquid to be tested, and to thereafter observe the changes in the test strip. In another approach, a droplet of the liquid is placed onto the test strip. The test strip is observed with an instrument structured and calibrated to make accurate measurements of the state of the test strip.

In one such approach, described in U.S. Pat. No. 4,935,346, a test strip is formed with a reagent layer affixed to an inert backing that has an aperture therethrough to a top side of the reagent layer. A droplet of a liquid to be analyzed, preferably blood in the case of the '346 patent, is placed in the aperture through the backing and thence onto the top side of the reagent layer. The blood is absorbed into the porous reagent layer, reacting with reagents previously introduced into the porous material of the reagent layer. The reagents include a dye that colors responsive to the presence of a particular active species in the liquid specimen.

As this test is performed, the test strip is held in a measurement instrument that directs a light beam against an opposite, second side of the porous reagent layer. The light reflected from the second side is measured over a period of time. Changes in the reflected light over this period quantitatively indicate the presence of the active species in the liquid specimen. The quantitative values obtained by this approach are usually not quite as accurate as those obtained by conventional wet chemical analysis. The test strip approach has the important advantage, however, that it can be used by a relatively unskilled person to obtain a close approximation of the amount of the active species present in the liquid specimen, with the testing performed in a home or other location away from a chemical laboratory.

This testing approach has been developed into a commercial product. However, several shortcomings in the test strips themselves and the methodology of the testing have been observed. From the standpoint of the user, the results obtained by the test instrument cannot be readily verified by visual inspection. From the standpoint of the designer of the test strip, the types of reagents and indicators are limited by the need to measure chemical changes in the presence of the various types of interference that are present. These disadvantages are also present in some other types of test strips, as well.

In one other approach of interest described in U.S. Pat. No. 4,477,575, a test strip is made with a separator layer of a material such as glass fiber that separates the blood applied thereto into two components, the plasma and the red blood cells. The separator layer overlies a reagent layer. A droplet of whole blood is applied to the top of the separator layer, the droplet is separated by percolation through the separator layer, and plasma emerges at the bottom of the separator layer. This plasma is absorbed into the reagent layer and reacted therein, with the reaction product observed visually or with an optical instrument. Interference with the chemical reaction of any active species in the plasma with the reagent layer due to the presence of the red blood cells in the whole blood is thereby removed entirely. While operable for some applications, the inventors have observed that this approach has the drawbacks in other applications that the rate of flow of the separated plasma is low and that the volume of percolate reaching the reactive layer is too small to be accurately measured.

There is a need for an improved test strip that overcomes the disadvantages of the available techniques, yet produces useful results. The present invention fulfills this need, and further provides related advantages.

SUMMARY OF THE INVENTION

The present invention provides a test strip and a method for its use. The test strip produces accurate, reproducible results. Interference from extraneous factors which are present in measurements using conventional test strips is greatly reduced or eliminated. In the case of measurements made on a colored specimen such as blood, the interference of the red coloring otherwise present is reduced to an acceptably low level, so that visual verification of the results is possible. The flow rate and volume of the measured specimen are maintained at a practical, high level. The elimination of the red coloring also permits the use of additional types of reagent systems than possible in conventional test strips. The test strip of the invention is not substantially more costly to produce than a conventional test strip. The test strip of the invention can be used interchangeably with other types of test strips in most cases.

In accordance with the invention, a test strip comprises a first layer with a first porous substrate having a first-layer chemical system impregnated therein. The first-layer chemical system comprises an indicator reagent, and, preferably, a reactive reagent. There is a flow-retarding layer comprising a differential flow-retarding material having a percolation rate for blood plasma faster than a percolation rate for red blood cells. The flow-retarding layer overlies the first layer and permits from about 10 to about 90 percent by volume of the red cells to pass therethrough in a period of 45 seconds. The flow-retarding layer can be made, for example, of glass fibers or polyester fibers. Preferably, an inert backing having an aperture therethrough overlies the flow-retarding layer.

When a droplet of blood is placed into the aperture of the backing, the droplet begins to percolate through the flow-retarding layer. The percolation rate of the red blood cells in the blood is retarded relative to that of the plasma, so that the fraction of the red blood cells in the percolate reaching the first porous substrate is reduced as compared with the fraction in the whole blood specimen. The chemical system of the first layer reacts with the glucose in the percolate, which is primarily plasma, and the color or other optically measurable feature of the first porous substrate is measured. Little glucose is present in the red blood cells, so the test results using the percolate are largely unchanged from those obtained by testing whole blood. However, because the visual interference produced by the red color of the red blood cells is partially removed from the percolate to an acceptably low level and thence is not present in the first porous substrate, the test results can be verified by visual inspection without interference from the strong red coloring that is otherwise present. A sophisticated measurement instrument is able to eliminate the interference from the presence of the red coloring when certain chemical systems are used, but the human eye does not have that capability. Reduction of the red-coloring interference allows the human eye to be employed as well, for verification or backup purposes.

The choice of chemical systems, including reagents and indicators, is limited for conventional test strips by the need to use a measurement instrument that can eliminate the effect of the intense red coloring normally present due to the full density of red blood cells. In the present approach, the reduction of the intensity of the red coloring allows other chemical systems to be employed. Such other chemical systems may be desirable in that they produce different chemical effects (a different color, for example) are more stable, are more sensitive, are more accurate, are less expensive to use, or have other benefits.

More generally, a test strip comprises an active structure with a top surface and a bottom surface. The active structure comprises a first layer having a first porous substrate with a first-layer chemical system impregnated therein, the first-layer chemical system comprising an indicator reagent, and desirably, a reactive reagent. The first layer has a top surface and a bottom surface which forms the bottom surface of the active structure. The test strip further has means for reducing the fraction of red blood cells in a whole blood specimen applied to the top surface of the active structure and percolated therethrough, such that the concentration of red blood cells in a percolate reaching the bottom surface of the active structure is from about 10 to about 90 percent of the concentration of red blood cells in the liquid specimen applied to the top surface of the active structure. An inert backing overlies the top surface of the active structure, and the backing has an aperture therethrough to the active structure.

The present invention provides an advance in the art of test strip technology. A portion of the red-cell content of the whole blood specimen is removed prior to performing a reaction and observing the reaction products, so that the intense red color of the initial concentration of the red cells does not interfere with the observation. Visual as well as instrumental observations of the reaction products can therefore be made. No additional treatment apparatus is required, so that knowledge of such apparatus and the ability to conduct a multiple-step procedure is not required of the person using the test strip. Other features and advantages of the present invention will be apparent from the following more detailed description of the preferred embodiment, taken in conjunction with the accompanying drawings, which illustrate, by way of example, the principles of the invention.

DETAILED DESCRIPTION OF THE INVENTION

The measurement of the glucose content of the blood is important for diabetics, and its measurement is the preferred utilization of the present invention. The glucose content of the blood can be measured by a technique such as that described in U.S. Pat. No. 4,935,346, whose disclosure is incorporated by reference. A specimen of whole blood is placed into the aperture of a test strip and allowed to react with the reactants provided in a reaction layer. The color change in the reaction layer, which is an indicator of the extent of the chemical reaction, is measured optically by reflection from the back side of the test strip in an instrument during a specific time period, 45 seconds in a commercial product, after a change of color is first detected in the reaction layer. The reaction product, which includes a dye whose change in coloration quantitatively indicates the glucose content of the blood, is obscured to some extent by the presence of an intense red coloring due to the red blood cells with which the reaction product is mixed.

The optical measurement instrument of the '346 patent operates at light wavelengths selected to avoid interference with the measurement by the red coloring. The indicator system is selected to cooperate with this technique. This approach is operable, but it does not permit the user of the testing procedure to visually verify the results because the human eye cannot operate to eliminate the source of interference. The capability to visually verify the results is desirable as a check that the measurement system has operated correctly and that the test strip used in the measurement is not defective. The selection of indicator systems is also limited to those which can cooperate with the approach selected for the optical measurement. It would be desirable to have the capability to use other indicator systems with improved properties.

The present invention provides an accurate glucose determination using the measurement instrument of the '346 patent from a whole blood specimen, while also permitting visual verification of the results and permitting the use of other indicator systems. The approach is based upon the recognition of the distribution of glucose in whole blood and the source of the interference. Whole blood is comprised of plasma and red blood cells. The glucose present in the blood resides primarily in the plasma component. In the present invention, the red blood cells are partially removed from the liquid sample, so as to partially negate the interference from the red coloration. The red blood cells are not entirely removed, because such a complete separation would require too long a period of time to be commercially acceptable and would also reduce the specimen volume to an unacceptably low level for accurate testing.

Figure 1:
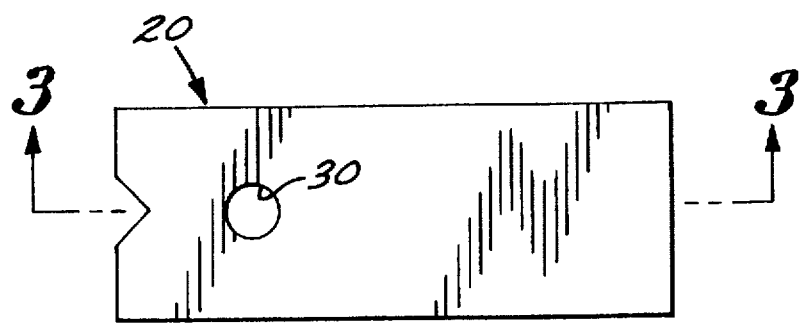
FIG. 1 is a top view of a test strip made according to the present invention.
Figure 2:
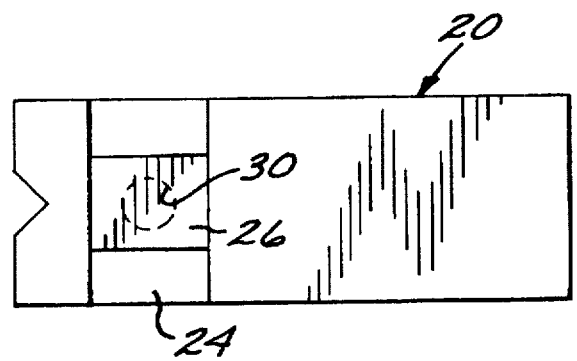
FIG. 2 is a bottom view of the test strip of FIG. 1.
Figure 3:
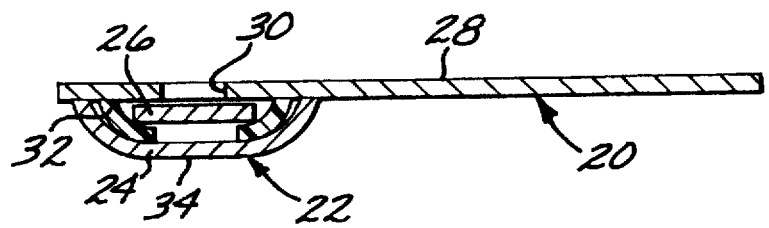
FIG. 3 is a side sectional view of the test strip of FIG. 1, taken generally along lines 3—3.

FIG. 1–3 depict a test strip 20 according to the invention. The test strip includes an active structure 22 having a first layer 24 and a flow-retarding layer 26 overlying the first layer 24. As used herein, "overlying" means that there is a registry and alignment of at least a portion of the referenced structures. "Overlying" permits the referenced structures, here the first layer 24 and the flow-retarding layer 26 to be spaced apart from each other, as shown in FIG. 3, or in physical contact with each other. An inert backing 28, which also serves as a test strip handle, is attached to and supports the active structure 22. The backing 28 has an aperture 30 therethrough in alignment with the flow-retarding layer 26 and the first layer 24. The flow-retarding layer 26 is preferably cut to a thin width so as to be just slightly larger than the size of the aperture 30, as shown in FIG. 2. A thin layer of adhesive 32 is placed between a portion of the flow-retarding layer 26 and a portion of the first layer 24 that are not aligned with the aperture 30, to hold the structure together and define a preferred gap between the layers 24 and 26 of several millimeters. In the use of the test strip 20, a droplet of a liquid specimen, such as whole blood, is placed into the aperture 30 on top of the flow-retarding layer 26. Liquid supplied from the specimen droplet flows through the flow-retarding layer 26 and thence to the first layer 24. The color of the test strip 20 is observed on an observation surface 34 (also called the "bottom surface") of the first layer 24.

As the droplet percolates through the flow-retarding layer 26, the percolation rate of the plasma component is greater than that of the red cell component. The flow-retarding layer 26 is made of a differential flow-retarding material which retards the flow rate of red blood cells more than it retards the flow rate of the plasma component of the blood. The differential flow-retarding material can be a glass-fiber containing layer, a polyester-containing layer, or other layer having these properties. In a preferred embodiment, the flow-retarding layer 26 is glass fiber paper having a thickness of from about 100 to about 240 micrometers, a basis weight of from about 20 to about 45 grams per square meter, and a mean pore size of from about 7 to about 9 micrometers. Such a material is available commercially from Whatman as glass paper, grade F132-01. Other differential flow-retarding materials can be used, such as glass fiber paper of different thicknesses, weights, and pore sizes, as long as the differential properties achieved as described subsequently.

The flow retarding-layer 26 is desirably formed of a material such as glass fiber or polyester with a pore size such that particles the size of red blood cells (about 8 micrometers in size) are retarded in their flow through the layer 26, as compared with the flow rate of blood plasma. This property renders the hemoglobin in these cells unable to interfere with the visualizing of the chemical reaction which takes place in the first layer 24.

The use of glass fiber to entirely separate whole blood into component parts prior to test-strip chemical determination is described in U.S. Pat. No. 4,477,575. This approach has not been found operable for use in glucose testing with the instrument of the '346 patent for two reasons. First, the complete separation requires too long a time to be operable in the instrument. Second, the complete separation reduces the volume of the specimen so much that the chemical determination becomes inaccurate. Instead, a flow-retarding approach for the red blood cells has been found to be sufficient to permit both visual verification and use of other indicator systems.

The first layer 24 is a hydrophilic, porous material impregnated with a first-layer chemical system. The hydrophilic, porous material of the first layer is preferably a piece of nylon-66 membrane having a thickness of about 0.005–0.0075 inches and lateral dimensions of about 0.3 by 0.6 inches. This porous substrate material is available commercially from Pall Corp. as Biodyne A. This material is made from nylon 66 and has a porosity size of about 5 micrometers. Other operable membranes having porosity sizes of from 0.45 to 5 micrometers include polysulfone membrane such as Thermopor membrane available from Gelman Scientific and polyether sulfone membrane such as Ultrabind membrane available from Gelman Sciences.

The first-layer chemical system includes at least an indicator reagent. Three indicator reagents have been found of most interest and are most preferred. The first indicator reagent is a mixture of 4-aminoantipyrine (AAP) and N-Ethyl-N-sulfohydroxypropyl-m-toluidine, sodium salt (TOOS) in a ratio of about 1 part by weight AAP to 4 parts by weight TOOS. The second indicator reagent is a mixture of AAP and N-ethyl-N-2 Sulfo ethyl m-Toluidine (ESET) in a ratio of about 1 part by weight AAP to 4 parts by weight ESET. The third indicator reagent is a mixture of 3-Methyl-2-benzothiazolinone hydrazone hydrochloride hydrate (MBTH) and TOOS in a ratio of about 1 part by weight MBTH to 4 parts by weight TOOS.

The first-layer chemical system also preferably includes a reactive reagent. The preferred reactive reagent for the measurement of blood glucose content is a mixture of glucose oxidase and peroxidase in a ratio of 2 parts by weight glucose oxidase to about 1 parts by weight of peroxidase. In another embodiment of the invention, the blood cholesterol content is measured using a reactive reagent which is a mixture of cholesterol esterase, cholesterol oxidase, and peroxidase in a ratio of 3 parts by weight cholesterol esterase, about 2 parts by weight cholesterol oxidase, and about 1 part by weight of peroxidase.

In the preferred approach wherein the indicator reagent and the reactive reagent are both present in the first-layer chemical system, a solution containing the indicator reagent, the reactive reagent, a binder and blocking agent, and a buffer is prepared. The preferred solution is an aqueous solution of from about 0.22 to about 0.86 grams per deciliter of the first component of the indicator reagent that is present as 1 part by weight, from about 0.8 to about 3 grams per deciliter of the second component of the indicator reagent that is present as about 4 parts by weight, about 0.86 grams per deciliter of glucose oxidase, about 0.54 grams per deciliter of peroxidase, 0.5 to 3 percent of gelatin and Gantrez polymer as binder and blocking agent respectively, and citric buffer or phosphate buffer, having a pH of 5–7, in a concentration of about 0.15 Molar. A most preferred dipping solution has 1.2 grams of gelatin, 0.6 grams of Gantrez polymer, 0.516 grams of AAP, 1.83 grams of TOOS, 103,200 I.U. of glucose oxidase, 59,200 I.U. of peroxidase, 18 milliliters of 1 molar citric buffer of pH 5, and 102 milliliters of distilled water. The hydrophilic, porous material of the first layer 24 is dipped into this solution at ambient temperature and thereafter dried.

Figure 4:
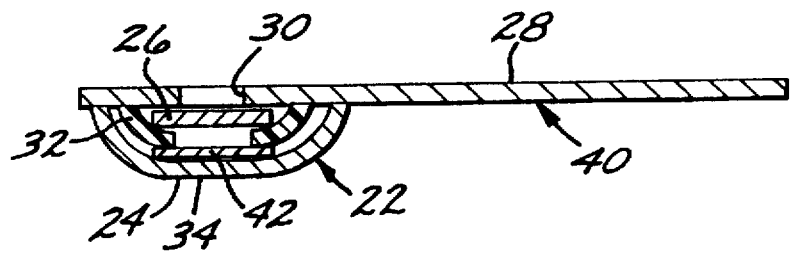
FIG. 4 is a sectional view of another embodiment of the test strip.

In an alternative approach illustrated in FIG. 4, a test strip 40 includes all of the structure described above for the test strip 20, and additionally includes a second layer 42 positioned between the first layer 24 and the flow-retarding layer 26 so as to overlie the first layer 24. The operable portions of the first layer 24, the second layer 42, and the flow-retarding layer 26 thus align and register with the aperture 30 of the inert backing 28. The second layer 42 is preferably made of the same hydrophilic, porous material as the first layer 24. In this embodiment, the first-layer chemical system includes only the indicator reagent, preferably the same indicator reagent as discussed previously. The second layer 42 includes a second-layer chemical system comprising only the reactive reagent, preferably the same reactive reagent as discussed previously. In this embodiment, the liquid which has percolated through the flow-retarding layer 26 encounters the second layer 42, where the component of the liquid to be measured reacts with the reactive reagent. The reaction product percolates through the second layer 42 into the first layer 24, where it further reacts with the indicator reagent to produce a measurable color change.

Figure 5:
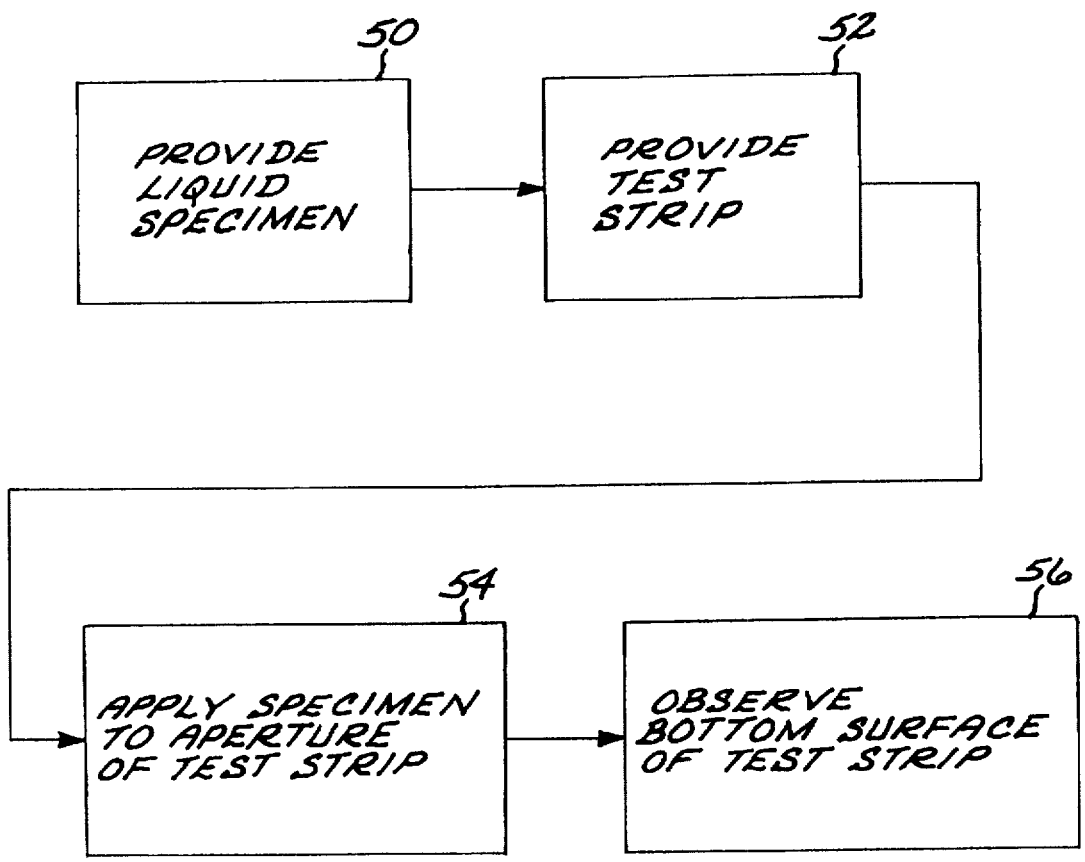
FIG. 5 is a block diagram of the approach of the invention.

FIG. 5 illustrates a preferred method for practicing the present invention. A liquid specimen, preferably whole blood, is provided, numeral 50. A test strip such as the test strip 20 or 40 is provided, numeral 52. The liquid specimen is applied to the aperture 30 of the test strip, numeral 54. The bottom, observation surface 34 of the test strip is observed for a color change indicating the presence of the chemical to be measured, numeral 56. The observation of color change can be performed with an instrument such as that of the '346 patent to obtain quantitative information, or visually to obtain semi-quantitative information. The latter semi-quantitative information is obtained by comparing the color on the bottom side 34 of the test strip with a standard color chart for various glucose (or other reactant) contents prepared and supplied by the manufacturer. Such a standard color chart is prepared by using known test solutions with the test strip to determine the color-change reaction. Thus, the user can obtain a visual backup for the instrument reading, or, in the case where no instrument is available, can obtain a semi-quantitative value (e.g., high, medium, low) for the content of the reactant in the blood. Using the present test strip in the absence of a proper instrument is not recommended, but may be necessary under some extreme circumstances.

In the complete absence of a flow-retarding layer 26, the observation (bottom) surface of the test strip is a bright red color, regardless of the extent of any reaction between the glucose in the specimen and the reagents and indicator system. The measurement instrument of the '346 patent can detect the extent of the reaction by performing wavelength-discriminating measurements. The human eye cannot perform such measurements, and therefore cannot be used to interpret the extent of the reaction visually. Where there is a separator layer as in the '575 patent so that no red cells reach the observation surface, no red blood cells reach the observation surface 34, but an insufficient volume of plasma reaches the first layer 24 in the required measurement time.

When the present approach is used, there is a balance between the reduction in red-cell content on the observation surface 34 and the total flow amount of plasma that reaches the first layer 24 and thence the observation surface 34. A sufficient amount of the red-cell content is removed so that the observation surface 34 has a background pinkish color which does not interfere with observation of color changes in the indicator of the first layer 24. The inventors have concluded, by visual analysis, that at least about 10 percent of the concentration of red cells in the specimen droplet should be retarded by the flow-retarding layer 26 so that they do not reach the observation surface 34 during the measurement period, which is 45 seconds after first color change on the observation surface 34 in the preferred approach. On the other hand, not all of red-cell concentration should be retarded, because this result has the effect of reducing the analysis volume of plasma reaching the first layer 24 by an unacceptable amount. From quantitative test results using the commercial measurement instrument, the inventors have concluded that no more than about 90 percent of the concentration of red blood cells in the specimen droplet should be retarded by the flow-retarding layer, so that they do not reach the observation surface 34 during the measurement period, which is 45 seconds after first color change on the observation surface 34 in the preferred approach.

The present approach permits more flexibility in the selection of indicator systems for use in the test strip. The indicator system of the '346 patent requires the use of organic solutions and aqueous solutions, whereas the three preferred indicator systems of the present invention require only aqueous solutions. The preparation of the test strips of the present invention is therefore less expensive and does not require the disposal of organic solvents. Various indicator colors are also potentially available. The AAP/TOOS indicator system changes to a purple color, the AAP/ESET indicator system changes to a purple color, and the MBTH/TOOS indicator system changes to a blue-purple color, as compared with the indicator system of the '346 patent, which changes to a purple color.

Figure 6:
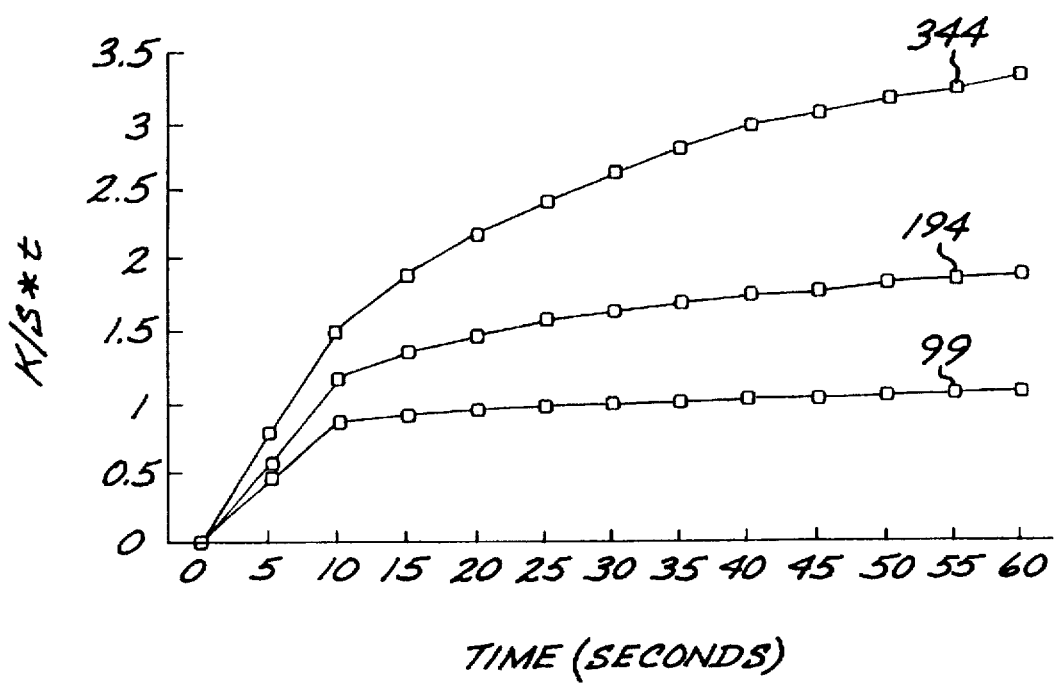
FIG. 6 is a graph of light absorbance as a function of time for a test strip according to the invention.
Figure 7:
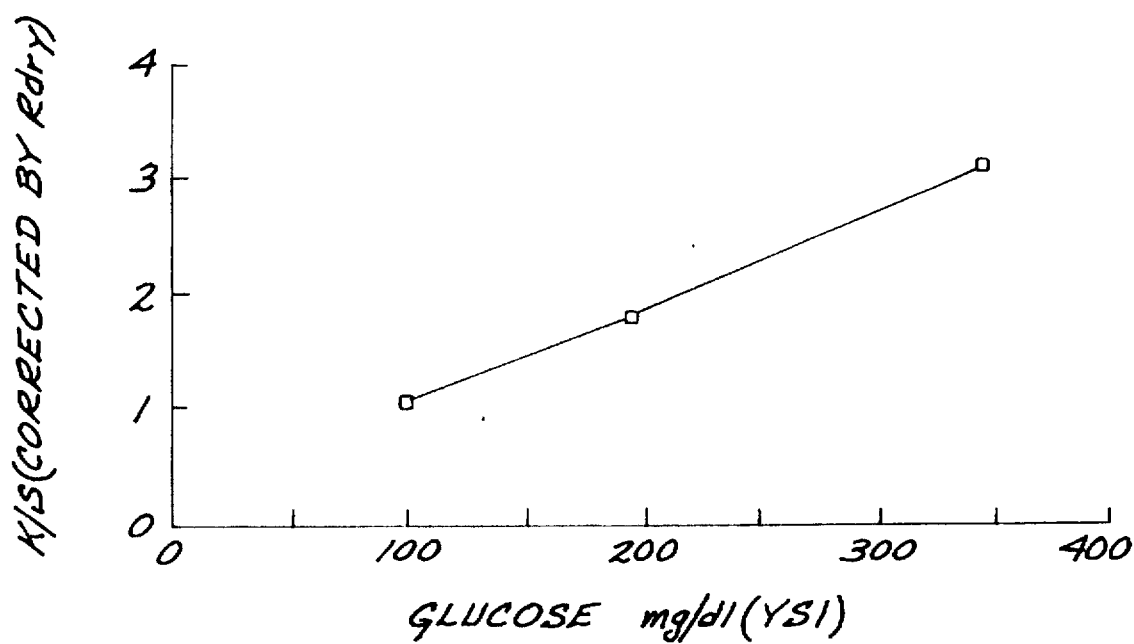
FIG. 7 is a standard curve of light absorbance as a function of glucose content of blood samples.

A number of test strips 20 were prepared using the glass-fiber flow-retarding layer, the AAP/TOOS indicator, and the glucose oxidase/peroxide reactive reagent in the manner discussed previously. In different tests, blood droplets having 99 milligrams per deciliter, 194 milligrams per deciliter, and 344 milligrams per deciliter of glucose were tested for glucose content. FIG. 6 is a graph of light absorbance K/S as a function of time after the observation surface 34 began changing color, in each case. FIG. 7 is a standard curve of absorbance determined over a defined time period of 45 seconds, according to the method of the '468 patent. By using this same approach, standard reference curves for any indicator/reactive reagent system can be determined.

Comparative testing of the effects of using the flow-retarding layer and not using the flow-retarding layer were performed. A test strip 20 was prepared using the glass-fiber flow-retarding layer, the AAP/TOOS indicator, and the glucose oxidase/peroxide reactive reagent in the manner discussed previously. An identical test strip was prepared for comparative purposes, except that it did not include the flow-retarding layer 26. The test strips with and without the flow-retarding layer 26 were tested with whole blood samples of three different glucose levels which were verified by accurate wet chemical techniques—a low glucose level of 104 milligrams per deciliter, an intermediate glucose level of 200 milligrams per deciliter, and a high glucose level of 360 milligrams per deciliter. The test strips were tested in an as-produced form. They were also tested after accelerated aging at 60 C. for 3, 5, and 7 days. These aging tests were conducted to evaluate the relative performance of the test strips after storage for extended periods of time, using this accelerated aging format.

Figure 8:
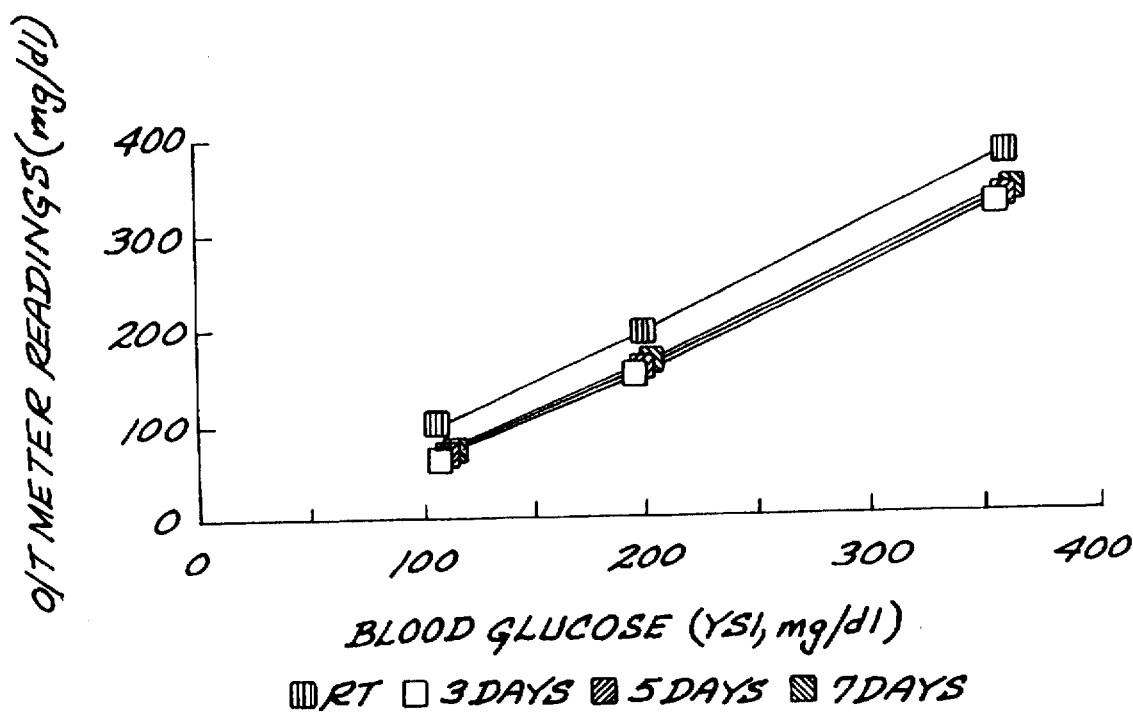
FIG. 8 is a graph showing stability of a test strip of the invention.
Figure 9:
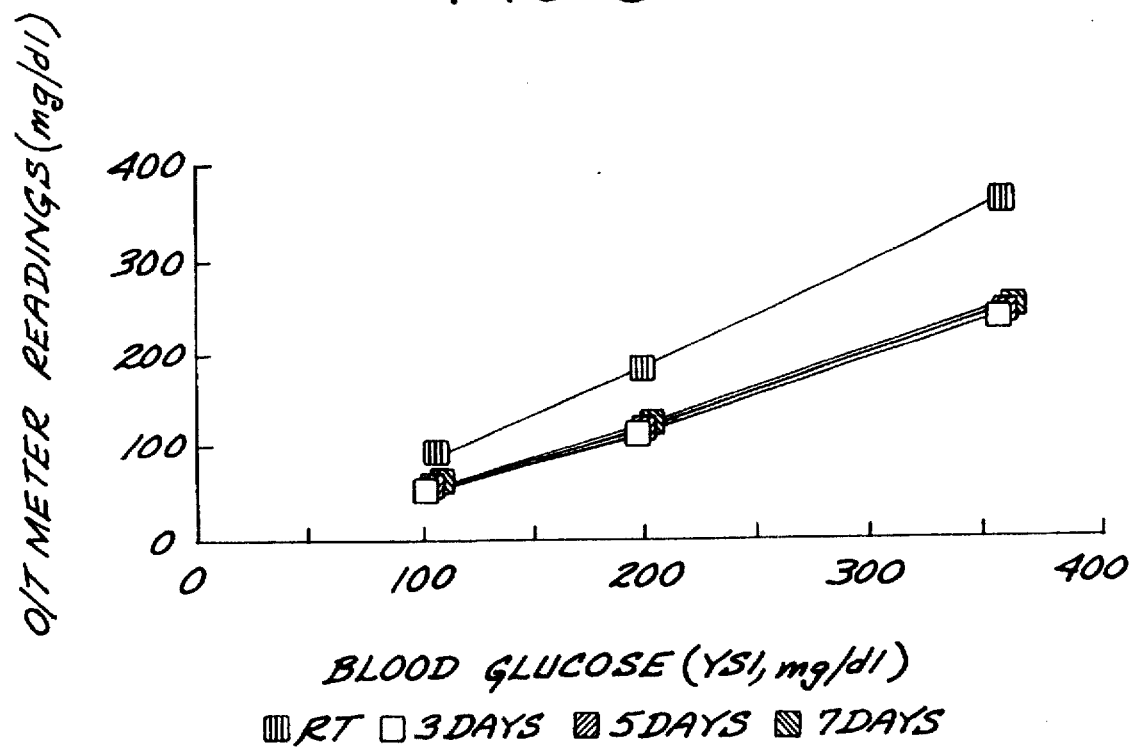
FIG. 9 is a graph of showing stability of a test strip of the invention under the same testing conditions as depicted in FIG. 6, except that no flow-retarding layer is present.

FIGS. 8 and 9 illustrate the results in graphical form. Both types of test strips gave reasonably accurate measured results for the unaged (as-prepared) test strips. Both types of test strips exhibited a decline in the measured results after aging. However, the test strips with the flow-retarding layer exhibited a smaller change in the measured values after accelerated aging. The test strips of the invention having a flow-retarding layer thus exhibit improved aging performance as compared with comparable test strips having no flow-retarding layer.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A test strip, comprising:

a first layer comprising a first porous substrate having a first-layer chemical system impregnated therein, the first-layer chemical system comprising an indicator reagent, wherein the indicator reagent comprises a mixture selected from the group consisting of (1) a mixture of 4-aminoantipyrine and N-ethyl-N-sulfohydroxypropyl-m-toluidine, sodium salt, (2) a mixture of 4-aminoantipyrine and N-ethyl-N-2 Sulfo ethyl m-Toluidine, and (3) a mixture of 3-Methyl-2-benzothiazolinone hydrazone hydrochloride hydrate and N-ethyl-N-sulfohydroxypropyl-m-toluidine, sodium salt; and a flow-retarding layer comprising a differential flow-retarding material having a percolation rate for blood plasma faster than a percolation rate for red blood cells, the flow-retarding layer overlying the first layer and permitting from about 10 percent to about 90 percent by volume of the red cells to pass therethrough in a period of 45 seconds.

2. The test strip of claim 1, further including an inert backing overlying the flow-retarding layer, the backing having an aperture therethrough to the flow-retarding layer.

3. The test strip of claim 1, wherein the first-layer chemical system further comprises a reactive reagent.

4. The test strip of claim 3, wherein the reactive reagent is selected from the group consisting of (1) a mixture of glucose oxidase and peroxidase, and (2) a mixture of cholesterol esterase, cholesterol oxidase, and peroxidase.

5. The test strip of claim 1, wherein the first porous substrate comprises a nylon membrane.

6. The test strip of claim 1, wherein the differential flow-retarding material comprises a layer of glass fibers.

7. The test strip of claim 1, wherein the differential flow-retarding material comprises a layer of a material selected from the group consisting of glass fibers and polyester fibers.

8. The test strip of claim 1, further including a second layer disposed between the first layer and the flow-retarding layer, the second layer comprising a second porous substrate having a second-layer chemical system impregnated therein, the second-layer chemical system comprising a reactive reagent.

9. The test strip of claim 1, wherein the flow-retarding layer comprises a flow-retarding layer glass fiber paper having a thickness of from about 100 micrometers to about 240 micrometers, a basis weight of from about 20 to about 45 grams per square meter, and a mean pore size of from about 7 to about 9 micrometers.

10. A test strip, comprising:

a first layer comprising a first porous substrate having a first-layer chemical system impregnated therein, the first-layer chemical system comprising an indicator reagent selected from the group consisting of (1) a mixture of 4-aminoantipyrine and N-ethyl-N-sulfohydroxypropyl-m-toluidine, sodium salt, (2) a mixture of 4-aminoantipyrine and N-ethyl-N-2 Sulfo ethyl m-Toluidine, and (3) a mixture of 3-Methyl-2-benzothiazolinone hydrazone hydrochloride hydrate and N-ethyl-N-sulfohydroxypropyl-m-toluidine, sodium salt, and a reactive reagent is selected from the group consisting of (1) a mixture of glucose oxidase and peroxidase, and (2) a mixture of cholesterol esterase, cholesterol oxidase, and peroxidase;

a flow-retarding layer comprising a differential flow-retarding material having a permeation rate for blood plasma faster than a permeation rate for red blood cells, the flow-retarding material comprising a glass fiber paper having a thickness of from about 100 micrometers to about 240 micrometers, a basis weight of from about 20 to about 45 grams per square meter, and a mean pore size of from about 7 to about 9 micrometers; and an inert backing overlying the flow-retarding layer, the backing having an aperture therethrough to the flow-retarding layer.

* * * * *